United States Patent
Neal et al.

(10) Patent No.: US 6,547,395 B1
(45) Date of Patent: *Apr. 15, 2003

(54) METHODS OF MEASURING MOVING OBJECTS AND REDUCING EXPOSURE DURING WAVEFRONT MEASUREMENTS

(75) Inventors: Daniel R. Neal, Tijeras, NM (US); Christopher Burak, Edgewood, NM (US); Daniel R. Hamrick, Cedar Crest, NM (US)

(73) Assignee: WaveFront Sciences, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/507,670

(22) Filed: Feb. 22, 2000

Related U.S. Application Data

(63) Continuation-in-part of application No. 09/244,680, filed on Feb. 4, 1999, now abandoned.
(60) Provisional application No. 60/074,337, filed on Feb. 6, 1998.

(51) Int. Cl.$^7$ .................................................. A61B 3/00
(52) U.S. Cl. ...................................................... 351/246
(58) Field of Search ............................... 351/205, 211, 351/212, 219, 221, 246, 247; 600/118; 607/7, 10, 11, 12, 13, 17, 88, 89, 130; 128/898; 356/121; 250/201.9, 208.1

(56) References Cited

U.S. PATENT DOCUMENTS

| | | |
|---|---|---|
| 3,819,256 A | 6/1974 | Bellows et al. |
| 4,021,102 A | 5/1977 | Iizuka |
| 5,258,791 A | 11/1993 | Penney et al. |
| 5,493,391 A | 2/1996 | Neal et al. ............... 356/121 |
| 5,777,719 A * | 7/1998 | Williams et al. ............ 351/212 |
| 5,929,970 A | 7/1999 | Mihaski |
| 6,052,180 A * | 4/2000 | Neal et al. ............... 356/121 |
| 6,095,651 A * | 8/2000 | Williams et al. ............ 351/246 |
| 6,270,221 B1 * | 8/2001 | Liang et al. ................ 351/221 |
| 6,271,914 B1 | 8/2001 | Frey et al. |
| 6,271,915 B1 | 8/2001 | Frey et al. |

FOREIGN PATENT DOCUMENTS

| | | |
|---|---|---|
| DE | 42 22 395 A1 | 1/1994 |
| EP | 0 373 788 A2 | 11/1989 |
| EP | 0 625 332 A2 | 4/1994 |
| WO | WO 83/02716 | 8/1983 |
| WO | WO 01/28408 A2 | 4/2001 |

OTHER PUBLICATIONS

Greivenkamp, J.E., and Bruning, J.H., Phase Shifting Interferometry, Optical Shop Testing, Second Edition, ISBN 0–471–522232–5, 1992, John Wiley & Sons, Inc.; pp. 501–598.

Neal, D.R., Armstrong, D.J. and Turner, W.T., Wavefront Sensors for Control and Process Monitoring in Optics Manufacture, reprinted from: Lasers as Tools for Manufacturing II, SPIE vol. 2993, LASE '97, Lasers and Applications, Photonics West, Feb. 13, 1997, pp. 1–10.

\* cited by examiner

*Primary Examiner*—George Manuel
(74) *Attorney, Agent, or Firm*—Volentine Francos, PLLC

(57) ABSTRACT

Metrology is performed using short, temporally resolved measurements in order to "freeze" the deformation of the object at a particular instant in time. The pulsed light beams are used to conduct metrology of moving objects and objects which are moved relative to the detector for measurement thereof. The motion may be translational, spiral and/or rotational. The duty cycle of the light source may be varied to in accordance with the control of the operation of the detector to perform metrology using a reduced total exposure of an object, while increasing the amount of light available for the measurement.

26 Claims, 2 Drawing Sheets

METHODS OF MEASURING MOVING OBJECTS AND REDUCING EXPOSURE DURING WAVEFRONT MEASUREMENTS

CROSS-REFERENCES TO RELATED APPLICATIONS

The present application is a continuation-in-part application under 35 U.S.C. §120 to U.S. patent application Ser. No. 09/244,680 filed on Feb. 4, 1999, now abandoned, allowed, entitled "Apparatus and Method for Characterizing Pulsed Light Beams," the entire contents of which are hereby incorporated by reference for all purposes, which in turn claims priority on U.S. Provisional Patent Application Serial No. 60/074,337 filed on Feb. 6, 1998.

BACKGROUND OF THE INVENTION

1. Field of the Invention

In the co-pending, commonly assigned application Ser. No. 09/244,680, an apparatus for measuring characteristics of pulsed light beams, primarily lasers, has been disclosed. The characteristics which are measured by the apparatus include phase, intensity, beam quality, $M^2$ factor, RMS wavefront error and other beam parameters. In the field of lasers and their applications, these parameters are of particular utility and interest.

The present invention is directed to use of pulsed wavefront sensors for applications in addition to measurement of pulsed lasers. In particular, the present invention is directed to using a pulsed wavefront sensor to measure moving elements, to simplify measurements involving moving parts, and to reduce exposure, particularly for use with biological systems.

2. Description of Related Art

In the optical metrology art, a surface to be measured, e.g., lens, mirror, wafer, metal of plastic film, disk platen, etc., is used as a reflector for a light beam. This reflected beam is measured with an optical sensor that measures the wavefront or phase of the beam. The phase measurement translates to a measurement to the surface of interest through one or more simple operations. While there are other, non-optical techniques for measuring surfaces, these do not have the particular advantages of speed, accuracy, dynamic range that will become apparent in this description. However, due to the requirement that other sources of relative motion, such as vibration, be eliminated between successive measurements, it is difficult to use optical metrology to measure characteristics of either moving objects or objects requiring relative motion between a sensor and the object for measurement thereof.

One example of optical metrology is the interferometric measurement of computer hard disk platens. For proper operation, the platen is to be as flat as possible to avoid collisions of the disk head with the surface of the platen. To test the platen, the disk platen is mounted in front of an interferometer or other wavefront or phase measuring device, and the characteristics of the light reflected therefrom are determined. For the case of an interferometer, this measurement requires four to six frames of images, where a reference mirror has been moved between images to provide a known phase shift. The data can then be interpreted and analyzed to produce the surface shape. Using these techniques, accuracy down to a few nanometers can be obtained.

However, in order to make accurate measurements, the disk platen must be held absolutely still between successive images. While this is possible using a vibration isolated platform for both the measuring instrument and the surface of interest, this stability requirement complicates, increases cost, and reduces the tolerance of the instrument to environmental effects. While there are other devices that can measure the wavefront or phase with fewer frames, these devices still have a finite measurement time.

If only the static deformations of the disk are of interest, then the interferometric techniques may be adequate. However, computer hard disk platens are spun at a high revolution rate. This can induce vibrations, modes, and surface shape changes that are only present during operation. With an interferometer or other prior art, these deformations can only be measured in an average sense.

Another example of measuring a moving object is the case of measuring an object that is larger than the aperture of the sensor. More details of this application are presented in co-pending, commonly assigned U.S. application Ser. No. 09/340,502 entitled "Apparatus and Method for Evaluating a Target Larger than a Measuring Aperture of a Sensor", which is hereby incorporated by reference in its entirety for all purposes. In this application, a large diameter mirror, wafer or other object is to be measured by a series of possibly overlapping measurements of the wavefront sensor. In this application, the position of the object or sensor is moved from one location to another on some form of motor controlled stage or scanning system. To measure the whole surface, many different positions of the stage must be realized, and an accurate measurement made in each case. The sequence of measurements is then pieced back together to form an overall measurement of the whole object.

A potential problem with this technique is that an accurate measurement must be made for each position of the object relative to the sensor. Thus the object must be moved to a new position, vibrations and oscillations must be damped out to an acceptable level, and then the wavefront sensor may acquire an image for analysis. For a mechanical stage (for example Dynamic Automated Systems model DAS AMB-300), this may take 100–300 ms for each new position, even when adjacent measurements are only 10 mm apart. This limits the total throughput of the measurement process, with the settling time being the dominant component.

Another use for wavefront measurement is in ophthalmic measurement. In ophthalmic measurement, a beam of light is projected into an eye to form a small spot on the retina. This spot is observed through an optical system to provide appropriate information for the wavefront sensor. In this type of measurement, it is desirable to minimize the total optical exposure of the eye and retina in order to avoid damage or discomfort to the patient under study. Thus the total exposure time should be kept to a minimum, as well as the total amount of energy delivered. The problem is that the retina is a fairly poor reflector of light. Furthermore, when using a Shack-Hartmann wavefront sensor, the return light is divided among a large number of focal spots for the. To improve the resolution of the measurement, it is desirable to divide the light among more focal spots. This leads to the need for more and more light to be projected to and received from the retina.

One characteristic of many modern CCD cameras, of particular concern when used for biological measurements, such as ophthalmic measurement, is that these cameras often have a separate exposure and read out time. During readout, the CCD element is not sensitive to light. Hence, CCD cameras they have a duty cycle that is less than 100%. A typical progressive scan CCD camera will have 5–50% duty cycle. This means that subject, e.g., an eye, is receiving exposure that is not necessary or useful for the measurement.

SUMMARY OF THE INVENTION

The present invention is therefore directed to using a wavefront sensor which substantially overcomes one or more of the problems due to the limitations and disadvantages of the related art.

It is an object of the present invention is to perform metrology using short, temporally resolved measurements in order to "freeze" the deformation of the object at a particular instant in time.

It is a further object of the present invention to perform metrology of even an extremely rapidly moving object.

It is a further object of the present invention to reduce the total exposure of an object while increasing the amount of light available for the measurement.

The above and other objects of the present invention may be realized by using a light source that may be pulsed or controlled temporally and a wavefront sensor capable of detecting such a light beam after having interacted with an object, particularly an object moving relative to the sensor. This combination can be used to optically measure a system, object or combination of elements in a temporally resolved fashion.

These and other objects of the present invention will become more readily apparent from the detailed description given hereinafter. However, it should be understood that the detailed description and specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other objects, aspects and advantages will be described with reference to the drawings, in which.

DETAILED DESCRIPTION OF THE PREFERRED EMBODIMENTS

Figure 1:
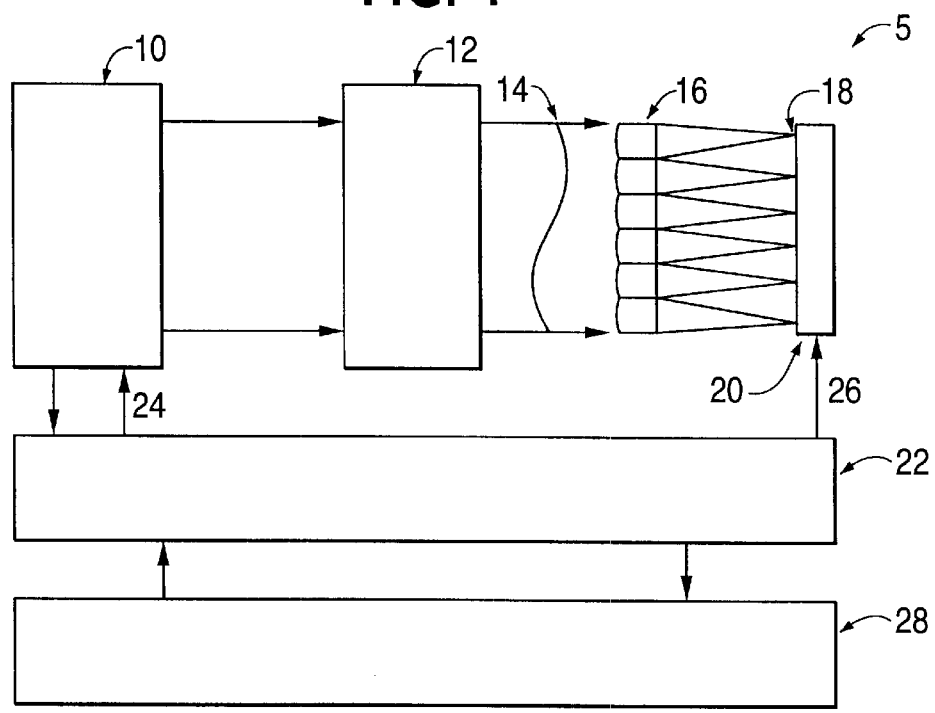
FIG. 1 is a schematic view of a pulsed wavefront sensor measurement of an optical system in accordance with the present invention.

The general use of a wavefront sensor to measure an object in accordance with the present invention is shown in FIG. 1. A light source 10 is used as a probe for the object under test 12. The light is reflected and/or transmitted by the object 12 as appropriate. The wavefront sensor 5 includes a lenslet array 16, a detector 20, and data acquisition electronics 22. The object 12 outputs an altered the wavefront or irradiance distribution 14. The resulting wavefront is divided with the lenslet array 16 to create a pattern of spots 18 on the detector 20. The detector 20 and the light source 10 are synchronized using the data acquisition electronics 22 and an electronic signal 24 from the light source 10 and an electronic signal 26 from the detector 20. The information is recorded and processed in a computer 28, which may be internal or external to the wavefront sensor 5.

To make measurements of the object 12 in motion in accordance with the present invention, a short duration pulse is used. Depending upon the desired speed of motion, the pulse length need to be adjusted to minimize blurring or smearing effects. Preferably, the pulse length is short enough so that the object has not moved relative to the sensor by more than a small fraction p, say 0.01 to 0.1 of the lenslet diameter. This will assure that an accurate measurement of the surface is made. Since the object is not necessarily the same size as the sensor, an optical system may be introduced between the various elements. The magnification of this optical system must be taken into account in determining the appropriate pulse length. For a system with magnification M between the object and the sensor, and lenslet diameter d and for an object traveling at velocity v, the pulse length τ should be arranged such that:

$$\tau < pd/Mv \tag{1}$$

Using a pulsed laser light source, such as a pulsed YAG or other laser, short pulses of light can be produced that last only a short duration. For example, a pulsed YAG laser typically has pulses that last 10 ns or less. As disclosed in the parent invention, such a source is synchronized with the wavefront sensor to allow measurement of pulsed beams. Thus, by using a pulsed light source and the pulsed wavefront sensor, the object under study may be measured while continuously moving relative to the sensor. This will result in much smoother motion of the object due to continuous motion rather than lots of stopping and starting. Thus, the light source 10, synchronized to the pulsed wavefront sensor 5, may be operated at a fixed frequency during the motion of the object. For an x-y scanned device, this means that continuous motion may be allowed in one dimension for the whole size of the part, with many measurements controlled by the stage position being acquired during the single scanned direction. At the end of one traverse, the direction is reversed and the next row or column is scanned. This can greatly speed up the measurement time. Similarly, measurement of objects having circular or spiral scanning or motion relative to the wavefront sensor may be realized.

Figure 2:
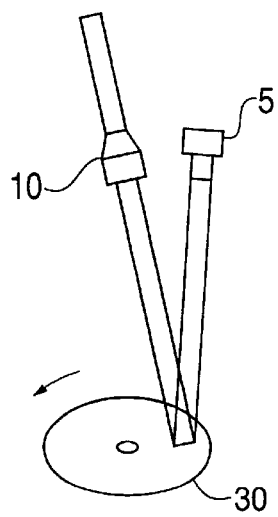
FIG. 2 is a schematic view of a pulsed wavefront sensor measurement of a moving object in accordance with the present invention.

FIG. 2 illustrates use of the wavefront sensor to measure a spinning hard disk drive 30. In this case, the light source 10 is arranged to be incident the disk platen surface 30 and the sensor 5 is arranged to detect light reflected from the disk platen surface 30. A pulse length short enough to minimize smearing is easily obtained by using a pulsed laser, such as a pulsed YAG laser (for example, a Big Sky Model ULTRA CFR-SHG). In this case, the pulse length τ is 10 ns. To measure a typical 3.5" disk drive, the sensor field of view must be 1.5 inches. For a typical 6.5×4.8 mm sensor, this means a magnification M of 0.16. With a typical lenslet diameter d of 0.144 mm, the maximum disk velocity (at the edge) would be 24.5 m/sec for 1% smearing. This translates to a revolution rate of 36,000 RPM. This significantly exceeds the revolution rate of any existing or planned disk drive.

Figure 3:
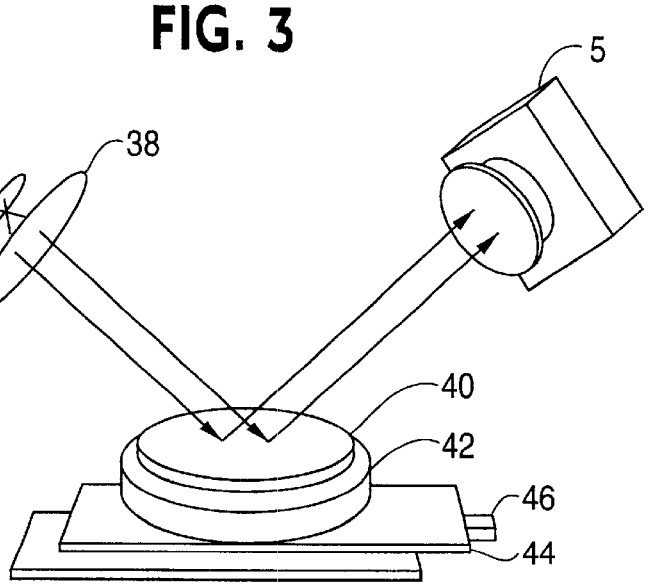
FIG. 3 is a schematic view of a pulsed wavefront sensor measurement of a wafer, flat panel display, or optic in accordance with the present invention.

FIG. 3 shows use of the wavefront sensor to measure a wafer, flat panel display, or optic 40. Preferably, a lens system 38 is used to expand the beam from the light source 10. In this case, the relative motion between the sensor 5 and the object 44 is due to the motion of a translation stage 44 and/or a rotation stage 42. These stages are used to scan the object which has an aperture larger than that of the sensor. In a other measurements of a large object, such as set forth in commonly assigned, co-pending U.S. application Ser. No. 09/340,502, the stage is moved and stopped between measurements. Sufficient time is required for motion or vibration to be damped out before measurement may be made. In contrast, use of a pulsed light source 10 with a wavefront sensor 5 allows the stages to be in continuous motion. Such continuous motion allows much faster and more accurate measurements to be made. In this case, a pulsed laser could be used, or even more simply, a diode or other controllable light source can be used to introduce a pulse with a short duty cycle. Equation (1) above can be used to estimate the maximum pulse length.

In a specific example, if the wavefront sensor 5 includes a lenslet array having 0.224 mm lenslets and a 1:1 magnification and the object 40 is moving at 300 mm/sec, up to 7.4 $\mu$s pulses may be used for 1% position smearing. With modern diode lasers, it is straightforward to modulate the source at this pulse width. In order to facilitate rapid acquisition and systematic information transfer between the computer and the camera/light source, a trigger source which is an external electronic circuit, instead of a software controlled circuit in the computer, may be advantageous. For the case of a moving stage, it may be extremely desirable to have the individual measurements recorded at a particular position of the stage. Many mechanical stages include the ability to have an encoder 46 with a precise position output (including the DAS AMB-300). Thus, such an encoder 46 can be set to provide a signal trigger every time the stage reaches a preset position. This will simplify the design of the software and other electronics, and minimize timing error and complexity in the computer.

Figure 4:
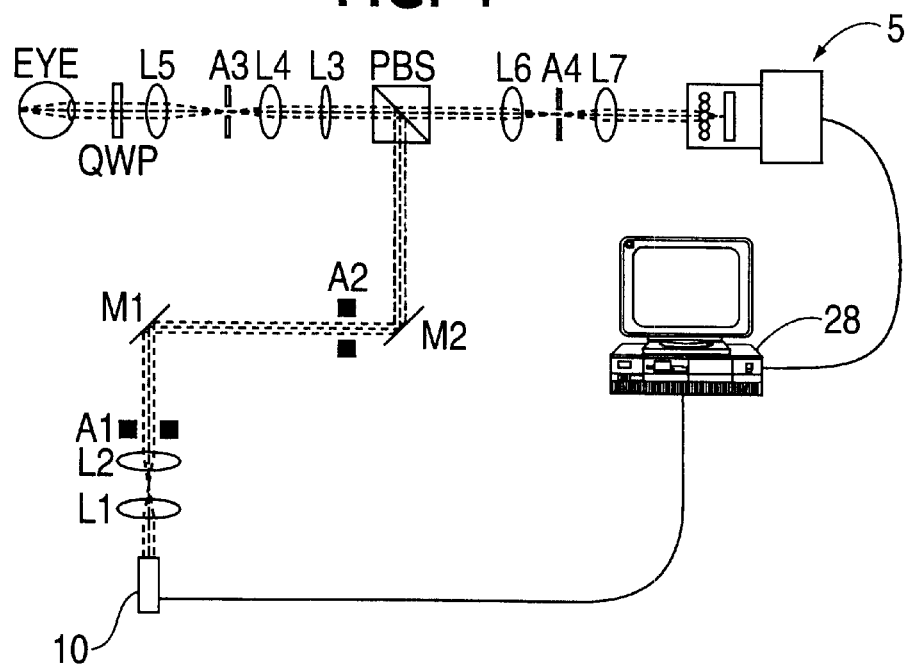
FIG. 4 is a schematic view of a system using a pulsed wavefront sensor to measure the human eye while reducing the total exposure by controlling the duty cycle of the pulsed light source in accordance with the present invention.

FIG. 4 is an example of a measurement of the human eye using a controllable light source and a pulsed wavefront sensor 5. In this case, a small diameter beam from a laser or super-luminescent diode (SLD) 10 is projected into the eye to create a small spot on the retina. In the specific example shown, the light is directed to the eye using a plurality of apertures A1–A3, a plurality of mirrors M1–M2, a plurality of lenses L1–L5, a polarizing beam splitter (PBS) and a quarter-wave plate (QWP). The light reflected by the eye is directed to the wavefront sensor 5 back through QWP, PBS, L3–L5 and A3, and through a plurality of lenses L6–L7 and another aperture A4.

To avoid discomfort for the patient, it is useful to use a near infrared beam which has minimum visibility by the patient. This also allows for a greater total power to be used. However, the maximum power that can be used is limited by safety limits, such as set forth in the ANSI Z136.1 standards. For typical conditions, this limits the total average power to less than 390 $\mu$w for a 10-sec exposure. For continuous exposure, the power limit is <250 $\mu$w. For best accuracy, high spatial resolution is desirable. To allow an adequate safety margin, the maximum practical exposure is ~100 $\mu$w. If a 0.144 diameter lenslet array is used with a system magnification of 0.68, 855 samples can be obtained across a 7.2-mm diameter pupil. The scattering efficiency of the retina is very low, ~0.1–0.5%. Thus the incident 100 $\mu$w is quickly reduced to ~0.2 nW per subaperture. While this is enough to detect with modern, sensitive, CCD cameras, it does not yield significant signal level, only 100–200 counts out of 1024.

A progressive scan camera has an exposure of only a portion of the frame time. The remaining portion is used to read out the CCD. Thus, in any frame there is always a portion of the time in which the sensor is not integrating light. If a continuous source is used, the light that is incident during the readout time is not used, and adds to the total exposure of the patient without yielding any additional signal on the camera. Using the pulsed wavefront sensor, the light may be turned on for only that portion of the frame time in which the sensor is active and accumulating charge. The safety limits apply primarily to the total integrated energy. By reducing the duty cycle of the exposure in conjunction with the camera, the total exposure is kept the same, while the peak power is increased by the inverse of the duty cycle. Thus, for a camera with 50% duty cycle with the light controlled to 50% duty cycle as well, the instantaneous power can be doubled while maintaining the same average power level. This would double the signal received by the camera and result in twice the amount of light on the sensor. For the low light levels of the eye measurement, a factor of two improvement is significant.

The duty cycle can be reduced further while still maintaining the same average power lever. This will allow a series of short "snapshot" images to be obtained for the measurement. This has the same advantages that are described previously for measuring a moving object, since living biological subjects are rarely stationary. For safety reasons, it may be advisable to configure the sensor so that the maximum power is still below the safety limits.

Figure 5:
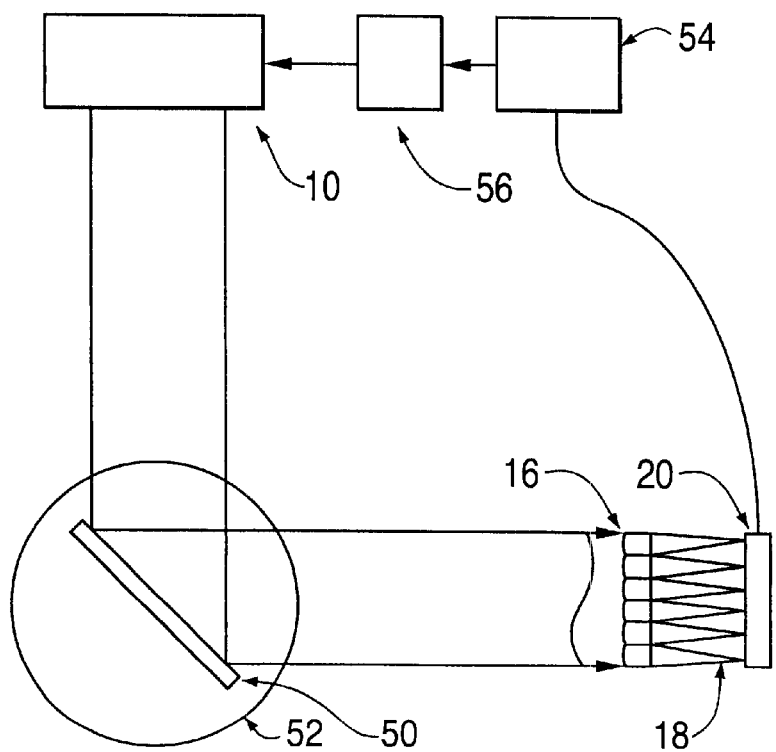
FIG. 5 is a schematic view of a system using the pulsed wavefront sensor of the present invention to measure dynamic modes of a scan mirror at operation speed in accordance with the present invention.

FIG. 5 shows the use a pulsed wavefront sensor 5 to test a laser scan mirror. One of the key limitations to the use of scanning mirrors at high speed is the introduction of dynamic modes in the mirror. These modes area function of the speed of oscillation, the shape of the mirror, its mass and moment of inertia, as well as the details of the connection to the shaft. The magnitude of these modes can be significant compared to the wavelength of light. Thus the mirror bending can introduce significant optical error into the reflected light. This greatly limits the performance of the system. This is a key limit on the speed at which such systems can be driven. To avoid the modal bending effects, the mirror must be made stiffer and thicker. This added mass greatly reduces the speed at which the system can be driven and increases the motor power requirements.

While these bending effects are a significant problem in themselves, the design and fabrication of a steering mirror system is further complicated by the fact that the bending effects are also extremely difficult to measure. The rapidly moving surface presents one face to a measurement system for only the smallest instant. Currently, since measurement has been impractical, the modes of the mirrors are determined only through finite element modeling. While some information can be obtained, this is very difficult because of the complexities of the connections and the several parts involved (mirror, mount, shaft, motor, motor mount, etc.). Even if a good model is constructed, verification of the model against experimental measurements is needed.

Using a short-pulse laser and the pulsed wavefront sensor in accordance with the present invention as shown in FIG. 5, the measurement of such a moving part is readily accomplished. A delay generator 56 is used to time the laser pulse to the correct orientation of the mirror 50, and then the laser and the wavefront sensor data acquisition is triggered. If the mirror is mounted in a rotary mount 52, then the measurement at different angles can be made by varying the delay to compensate for the mirror position. This measurement is only possible with a device such as the pulsed wavefront sensor because of its ability to make wavefront measurements in a single snapshot, synchronized to a pulsed light source.

As shown in FIG. 5, the controllable light source 10 is expanded and directed onto the surface of the scan mirror 50 that is mounted in an adjustable mount 52. The mount 52 allows adjustment of the angular position of measurement independent from the scan angle of the mirror 50. The light reflected off the mirror 50 impinges on the lenslet array 16 and creates focal spots 18 (also known in the art as aerial images) on the detector 20. The computer and data acquisition electronics 54, here provided together, controls and acquires data such that the scan mirror 50 is in the proper position to illuminate the detector 20 when the pulsed light source 10 is triggered. The delay generator 56 delays the trigger pulse to the appropriate time so that the mirror 50 is in the right position. Different positions of the scan mirror 50 may be measured by adjusting the rotating mount 52, and then choosing the appropriate delay.

Using this apparatus and method, the modes of the scan mirror 50 may be completely characterized and tested, at a number of different positions of the scan mirror. This measurement will require the use of short laser pulses for most effective operation.

While the present invention is described herein with reference to illustrative embodiments for particular applications, it should be understood that the present invention is not limited thereto. Those having ordinary skill in the art and access to the teachings provided herein will recognize additional modifications, applications, and embodiments within the scope thereof and additional fields in which the invention would be of significant utility without undue experimentation. Thus, the scope of the invention should be determined by the appended claims and their legal equivalents, rather than by the examples given.

What is claimed is:

1. A method for performing metrology on an object comprising:
    controlling a light source to output a pulsed light beam;
    providing the pulsed light beam to the object;
    dividing the pulsed light beam having interacted with the object into a plurality of spots;
    controlling operation of a detector in accordance with a synchronization pulse from the light source, the detector converting the plurality of spots into electronic signals;
    synchronizing data acquisition electronics to the light source and the detector, the data acquisition electronics integrating the electronic signals from the detector for a single pulse from the light source; and
    computing characteristics of the pulsed light beam having interacted with the object in a single pulse from integrated electronic signals.

2. The method of claim 1, wherein said controlling of the light source results in a pulsed light beam of short duration.

3. The method of claim 1, further comprising moving the detector and the object relative to one another.

4. The method of claim 3, wherein, when the object is larger than the aperture of the detector, relative movement between the object and the detector is continuous.

5. The method of claim 4, wherein the object is one of a silicon wafer, a flat panel display, an optic, and a disk drive platen.

6. The method of claim 3, wherein the relative movement is in along a single axis.

7. The method of claim 3, wherein the object is one of a moving disk platen, an optical disk, a holographic storage disk, and an optic.

8. The method of claim 3, wherein the object is a film of one of metal, glass and plastic.

9. The method of claim 3, further comprising delaying operation of the detector in accordance with a position of the object.

10. The method of claim 3, further comprising timing operation of the detector in accordance with preset encoder signals.

11. The method of claim 10, wherein, when the object is larger than the aperture of the detector, relative movement between the object and the detector is continuous.

12. The method of claim 3, wherein said moving includes relative translation of at least one of the x and y positions.

13. The method of claim 3, wherein said moving includes relative circular motion.

14. The method of claim 3, wherein said moving includes relative spiral motion.

15. The method of claim 1, further comprising controlling total exposure of the object by varying the duty cycle of the light source.

16. The method of claim 15, wherein the object is biological.

17. The method of claim 15, wherein the object is an eye.

18. The method of claim 1, including placing the detector in a fixed mount.

19. A method of determining wave aberrations of the eye, comprising:
    providing pulsed light to produce a light spot on a retina of an eye;
    receiving an image of light backscattered from the light spot on the retina of the eye and for creating aerial images of the light spot;
    detecting the aerial images from the lenslet array; and
    determining wave aberrations of the eye from the aerial images.

20. The method of claim 19, wherein determining wave aberrations of the eye from the aerial images comprises:
    converting the detected aerial images into electronic signals; and
    computing the wave aberrations using the electronic signals.

21. The method of claim 19, further comprising controlling a pulsed light source to provide the pulsed light in synchronization with detecting the aerial images.

22. A wavefront sensor for determining the wave aberrations of the eye comprising:
    a lenslet array adapted to receive an image of light backscattered from a light spot on a retina of the eye and for creating aerial images of the light spot;
    a detector adapted to receive the aerial images from the lenslet array; and
    a pulsed light source adapted to provide light to the retina and to increase a peak intensity of the light for forming the aerial images,
    wherein the detector is synchronized with the pulsed light source.

23. The wavefront sensor of claim 22, further comprising a processor adapted to receive signals from the sensor corresponding to the aerial images and to determine the wave aberrations from the signals.

24. The wavefront sensor of claim 22, further comprising a $\lambda/4$ waveplate in an optical path of the wavefront sensor.

25. The wavefront sensor of claim 22, further comprising a polarizing beamsplitter in an optical path of the wavefront sensor.

26. The wavefront sensor of claim 22, wherein the pulsed light source comprises a pulsed laser.

* * * * *